(12) United States Patent
Ahearn et al.

(10) Patent No.: US 10,067,128 B2
(45) Date of Patent: Sep. 4, 2018

(54) CELL-BOUND COMPLEMENT ACTIVATION PRODUCT ASSAYS AS COMPANION DIAGNOSTICS FOR ANTIBODY-BASED DRUGS

(71) Applicant: Allegheny-Singer Research Institute, Pittsburgh, PA (US)

(72) Inventors: Joseph M. Ahearn, Wexford, PA (US); Chau-Ching Liu, Pittsburgh, PA (US); Susan M. Manzi, Wexford, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 0 days.

(21) Appl. No.: 15/223,906

(22) Filed: Jul. 29, 2016

(65) Prior Publication Data

US 2017/0030905 A1 Feb. 2, 2017

Related U.S. Application Data

(60) Provisional application No. 62/199,713, filed on Jul. 31, 2015.

(51) Int. Cl.
*G01N 33/564* (2006.01)
*G01N 33/86* (2006.01)
(Continued)

(52) U.S. Cl.
CPC ....... *G01N 33/564* (2013.01); *G01N 33/5052* (2013.01); *G01N 33/86* (2013.01);
(Continued)

(58) Field of Classification Search
CPC .............. G01N 33/564; G01N 33/5091; G01N 33/5055; G01N 33/505; G01N 33/5052; G01N 33/5047; G01N 33/536; G01N 33/6854; G01N 33/7095; G01N 2800/104; G01N 2800/7095; G01N 2333/7051; G01N 2333/70517; G01N 33/86; G01N 2800/52; G01N 2333/4716; G06F 19/345; G06F 19/20; G16H 50/20
See application file for complete search history.

(56) References Cited

U.S. PATENT DOCUMENTS 7,390,631 B2 6/2008 Ahearn et al.
7,585,640 B2 * 9/2009 Ahearn ................ G01N 33/564
435/287.2
(Continued)

FOREIGN PATENT DOCUMENTS

WO 2010/045611 A2 4/2010
WO 2011047337 A2 4/2011
(Continued)

OTHER PUBLICATIONS

U.S. Appl. No. 15/264,516, filed Feb. 2017, Ahearn; Joseph M.*
(Continued)

*Primary Examiner* — Gailene Gabel
(74) *Attorney, Agent, or Firm* — Fox Rothschild LLP

(57) ABSTRACT

Methods, systems, and kits useful for determining whether a subject is likely to benefit from therapy with an antibody are provided. In particular aspects, cell-bound complement activation products (CB-CAPs) associated with B lymphocytes may serve as diagnostic biomarkers.

10 Claims, 2 Drawing Sheets

(51) Int. Cl.
*G01N 33/50* (2006.01)
*G16H 50/20* (2018.01)
*G06F 19/00* (2018.01)

(52) U.S. Cl.
CPC .............. *G06F 19/00* (2013.01); *G16H 50/20* (2018.01); *G01N 2333/4716* (2013.01); *G01N 2800/52* (2013.01)

(56) References Cited

U.S. PATENT DOCUMENTS

| | | | |
|---|---|---|---|
| 7,588,905 | B2 | 9/2009 | Ahearn et al. |
| 8,080,382 | B2 | 12/2011 | Ahearn et al. |
| 8,126,654 | B2 | 2/2012 | Ahearn et al. |
| 9,075,069 | B2 | 7/2015 | Weber et al. |
| 9,495,517 | B2 * | 11/2016 | Ahearn ................ C12Q 1/6883 |
| 2005/0042602 | A1 | 2/2005 | Ahearn et al. |
| 2006/0280738 | A1 * | 12/2006 | Tedder ................... A61K 38/13 424/141.1 |
| 2010/0233752 | A1 | 9/2010 | Ahearn et al. |
| 2012/0052066 | A1 | 3/2012 | Calderon et al. |
| 2013/0309698 | A1 * | 11/2013 | Dervieux ............. G01N 33/564 435/7.92 |
| 2015/0339449 | A1 | 11/2015 | Ahearn et al. |
| 2016/0041164 | A1 | 2/2016 | Ahearn et al. |
| 2016/0333082 | A1 * | 11/2016 | Wiestner ................ C07K 16/18 |

FOREIGN PATENT DOCUMENTS

| | | |
|---|---|---|
| WO | 2012109592 A1 | 8/2012 |
| WO | 2014020357 | 2/2014 |
| WO | 2014093268 A1 | 6/2014 |
| WO | 2014124098 A1 | 8/2014 |
| WO | 2015/105973 | 7/2015 |

OTHER PUBLICATIONS

Ahearn et al., "Biomarkers for Systemic Lupus Erythematosus," Translational Research, Feb. 10, 2012, vol. 159, pp. 326-342 (Abstract only).
Ahearn et al., "The Lupus Biomarker Odyssey: One Experience," Methods in Molecular Biology (Clifton, NJ) Jan. 2014, vol. 1134, pp. 14-35. (abstract).
Bentwich et al., "Specific Properties of Human B and T Lymphocytes and Alterations in Disease," Transplant. Rev., 1973, vol. 16, pp. 29-50. (Abstract).
Kalunian, K. C. et al., "Measurement of Cell-Bound Complement Activation Products Enhances Diagnostic Performance in Systematic Lupus Erythematosus," Arthritis & Rheumatism, vol. 64, No. 12, Dec. 1, 2012, pp. 4040-4047.
Li et al., "Antilymphocyte Antibodies in Systemic Lupus Erythematosus: Association with Disease Activity and Lymphopenia," Journal of Immunology Research, Apr. 17, 2014, vol. 2014, Art ID 672126, 6 pages.
Li, Q.-Z. et al., "Interferon Signature Gene Expression is Correlated with Autoantibody Profiles in Patients with Incomplete Lupus Sundromes," Clinical and Experimental Immunology, vol. 159, No. 3, Mar. 1, 2010, pp. 281-291.
Liu et al., "Antilymphocyte Autoantibodies Generate T Cell-D4d Signatures in Systemic Lupus Erythematosus," Trans Res., Dec. 2014, vol. 164, No. 6, pp. 496-507. DOI: 10.1016/j. trsl 2014-07-007.Epub Aug. 7, 2014 (Abstract).
Liu et al., Biomarkers in Systemic Lupus Erythematosus: Challenges and prospects for the future,: Therapeutic Advances in Musculoskelatal Disease, Aug. 1, 2013, vol. 5, No. 4, pp. 210-233.
Liu et al., "Cell-Bound Complement Biomarkers for Systemic Lupus Erutyhematosus: From Benchtop to Bedside," Rheum Dis Clin N Am, Feb. 1, 2010, vol. 36, pp. 161-172.
Liu et al., "Complement C4d Deposition on T Lympocytes: Mechanisms and Significance in Systemic Lupus Erythematodud (SLE)," Molecular Immunology, 2007, vol. 44, pp. 147-266.
Liu, Chau-Ching et al. "Complement C4d deposition on circulating Blood Cells: Mechanisms and Implication in Systemic Lupus Erythematosus (SLE)," Molecular Immunology, Aug. 2010, vol. 47, No. 13, Supp. 4, pp. 2286.
Liu et al., "Lymphocyte-Bound Complement Activation Products as Biomarkers for Diagnosis of Systemic Lupus Erthematosus," Clinical Translation Science, Aug. 1, 2009, vol. 2, Issue 4, pp. 300-308.
Liu, Chau-Ching et al., "Lymphocyte-Bound Complement Activation Products (LB-CAP) as Biomarkers for SLE," Lupus, Jun. 2010, vol. 19, Supp. 1, pp. 54.
Liu et al., "Reticulocytes Bearing C4d as Biomarkers of Disease Activity for Systemic Lupus Erthematosus, Arthritis Rheumatism," vol. 52, No. 10, Oct. 2005, pp. 3087-3099.
Liu Chau-Ching et al., "Session Title: Systematic Lupus Erythematosus—Human Etiology and Pathogenesis Poster I Session Type: ACR Poster Session A Cell-Bound Complement Activation Products (CB-CAP) Profiles in Patients with Pre-Systemic Lupus Erythematosus," Sep. 29, 2015.
Manzi et al., Measurement of Erythrocyte C4d and Complement Receptor 1 in Systemic Lupus Erythematosis,: Arthritis Rheumatism, Nov. 2004, vol. 50, No. 11, pp. 3596-3604.
Navratil et al., "Platelet-C4d is Highly Specific for Systemic Lupus Erythematosus," Arthritis Rheumatism, vol. 54, No. 2, Feb. 2006, pp. 670-674.
Olsen, N.J. et al., "Biomarker-Driven Assessment of Lupus Progression," Sep. 18, 2012, printed from Internet, http://www.lupus.org/reserach-news/entry/biomarker-driven-assessment-of-lupus-progress . . . Jul. 20, 2015.
Pickering et al., "Links Between Complement Abnormalities and Systemic Lupus Erythematosus," Rheumatology, Jan. 1, 2000, vol. 29, pp. 133-141.
Reininger et al., "T Helper Cell Subsets in the Pathogenisis of Systemic Lupus Erythematosus," Ann Med Interne, 1996, vol. 147, No. 7, pp. 467-471 (Abstract only).
Vila, L.M. et al., "Clinical Outcome and Predictors of Disease Evolution in Patients with Incomplete Lupus Erythematosus," Lupus, Sage, GB, vol. 9 No. 2, Jan. 1, 2000, pp. 110-115.
"What is Lupus and How Does it Affect the Body?" From 2012 Lupus Educational Series, pp. 1-4, Jan. 18, 2013; http://lupusny.org/news/foundation-news/2013/01/18/what-lupus-and-how-does-it-affect-body.
Winchester et al., "Analysis of Lymphocytes from Patients with Rheumatoid Arthritis and Systemic Lupus Erythematosus," The Journal of Clinical Investigation, Nov. 1974, vol. 54, pp. 1082-1092.
International Search Report and Written Opinion dated Nov. 15, 2016, issued in Application No. PCT/US2016/044779.

\* cited by examiner

CELL-BOUND COMPLEMENT ACTIVATION PRODUCT ASSAYS AS COMPANION DIAGNOSTICS FOR ANTIBODY-BASED DRUGS

CROSS-REFERENCE TO RELATED APPLICATION

This application claims the benefit of U.S. Provisional Patent Application No. 62/199,713, filed Jul. 31, 2015, titled "Cell-Bound Complement Activation Products Assays as Companion Diagnostics for Antibody-Based Drugs," the disclosure of which is hereby incorporated by reference herein in its entirety.

BACKGROUND

Monoclonal antibody drugs bind to specific antigens on target cells. In some cases, once attached to their antigens, the drugs stimulate the patient's immune system to attack the labeled cells. In other cases, the mechanism of therapeutic action that follows binding remains unknown. Rituximab, a monoclonal antibody that targets a specific antigen (CD20) on B-cells has become a common therapeutic for patients with B-cell lymphoma; it is also being used to treat systemic lupus erythematosus (SLE) and other autoimmune disorders. There are additional monoclonal antibody drugs in development that target B-cell antigens, including CD20 and other surface expressed antigens.

SUMMARY

This document identifies, in certain aspects, methods, systems and kits useful for determining whether a subject is likely to benefit from therapy with an antibody by measuring, in a blood sample containing white blood cells from the subject, a level of a diagnostic biomarker associated with a surface of a B lymphocyte in the sample.

BRIEF DESCRIPTION OF THE DRAWINGS

FIG. 1A illustrates data from four patients with Systemic Lupus Erythematosus (SLE). FIG. 1B illustrates data from twelve healthy controls.

DETAILED DESCRIPTION

Figure 1A:
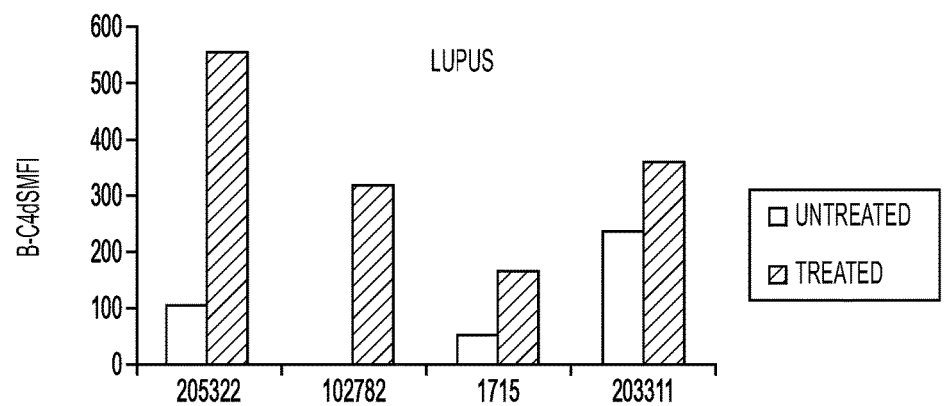
FIGS. 1A and 1B illustrate specific median fluorescence intensity (SMFI) (Y-axis) achieved when labeled and unlabeled B-cells were treated with plasma containing antibodies and a source of complement, demonstrating that B-cells from different patients (X-axis) were effectively labeled with C4d as a result of complement activation.

The disclosure of the following patent document is incorporated herein by reference: U.S. Pat. No. 7,585,640, issued Sep. 8, 2009, titled "Diagnosing and Monitoring Inflammatory Diseases by Measuring Complement Components on White Blood Cells."

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

A "cell-bound complement activation product" or "CB-CAP" is a combination of one or more complement activation products and a blood cell (including, but not limited to, an erythrocyte, reticulocyte, T lymphocyte, B lymphocyte, monocyte, granulocyte or platelet) to which the complement activation product is bound.

As used in this document, a "control" level of any CB-CAP refers, in some embodiments, to a level of that CB-CAP obtained from a sample obtained from one or more individuals who do not suffer from the autoimmune, inflammatory or other disease or disorder that is of interest in the investigation. The level may be measured on an individual-by-individual basis, or on an aggregate basis such as an average. A "control" level can also be determined by analysis of a population of individuals who have the disease or disorder but are not experiencing an acute phase of the disease or disorder. A "control" cell or sample may be used to obtain such a "control" level. A "control" cell or sample may be obtained from one or more individuals who do not suffer from the autoimmune, inflammatory or other disease or disorder that is of interest in the investigation. A "control" cell or sample can also be obtained from of a population of individuals who have the disease or disorder but are not experiencing an acute phase of the disease or disorder.

In some embodiments, a "control" level of a respective CB-CAP, cell or sample is from the same individual for whom a diagnosis is sought or whose condition is being monitored, but is obtained at a different time. In certain embodiments, a "control" level, sample or cell can refer to a level, sample or cell obtained from the same patient at an earlier time, e.g., weeks, months, or years earlier.

As used in this document, "a difference from a control level" refers to a difference that is statistically significant, as determined by any statistical analysis method now or hereafter used by those in the art. A difference from a control level refers to a statistically significant difference between a control level of a respective CB-CAP and a level of the same CB-CAP from an individual for whom diagnosis or other information is sought, i.e., an experimental level. Those of skill will recognize that many methods are available to determine whether a difference is statistically significant and the particular method used is not limiting to the invention.

As used herein a "white blood cell" refers to circulating blood cells that are not erythrocytes, megakaryocytes, circulating endothelial cells, or reticulocytes; for example, T and B lymphocytes, NK cells, eosinophils, basophils, granulocytes, neutrophils, monocytes, macrophages, plasma cells, and stem cells.

As used herein, a peripheral blood mononuclear cell (PBMC) can correspond to any blood cell having a round nucleus. Such cells are known to play a role in the immune response. PBMC may include, for instance, lymphocytes such as T lymphocytes, B lymphocytes and NK cells, monocytes and macrophages.

For the purposes of this document, an "electronic device" or "processing device" refers to a device that includes a processor and a non-transitory, computer-readable memory. The memory may be integral to the device, or it may be remote from the device and accessible by the device via one or more communication networks. The memory may contain programming instructions that, when executed by the processor, are configured to cause the processor to perform one or more operations according to the programming instructions. Examples of electronic devices include computing devices, tablets, and smart phones.

As used herein, the term "subject" is used to mean an animal, including, without limitation, a mammal. The mammal may be a human. The terms "subject" and "patient" may be used interchangeably.

The presence of cell-bound complement activation products (CB-CAPs) on white blood cells has previously been observed. The present inventors have demonstrated that the presence of cell-bound complement activation products on B-cell antigens can affect the binding affinity of antibodies to their targets.

Assays that detect the presence, surface density, and/or nature of complement proteins on the surface of B-cells may be used to predict the potential therapeutic benefit and/or required dosage of a particular monoclonal antibody drug. Such assays may also be valuable in selecting from an array of monoclonal antibody drugs that target different antigens or different locations on a particular antigen. Assays that measure CB-CAPs on the surface of a patient's B-cells may be used to determine what drug and dosage may be most relevant for the particular patient.

In embodiments, methods, systems and kits are provided for detecting and, optionally, quantifying the level of a diagnostic biomarker associated with a surface of a B lymphocyte cell obtained from a blood sample. In embodiments, a blood sample contains white blood cells. In embodiments, at least one biomarker is a CB-CAP. In embodiments, at least one biomarker is selected from the group consisting of C4d, C3d, C4b, iC4b, C3b, iC3b, and C3dg, all of which are peptides that may be generated by complement activation.

In embodiments, the methods, systems, and kits may involve the detection of a cell-surface marker for B lymphocytes. In embodiments, the cell-surface marker for B lymphocytes may be selected from the group including, but not limited to, CD5, CD19, CD20, CD21, CD22, CD23, CD25, CD40, CD69, CD70, CD79, CD80, CD85, CD86, CD137, CD138, CD252, and CD268.

The detection methods described herein can be carried out manually, but often are conveniently carried out using an automated system and/or equipment, in which the blood sample or an isolated blood cell fraction, such as, without limitation, peripheral blood leukocytes (PBLs), is analyzed automatically to make the necessary determination or determinations, and the comparison with the base or reference value is carried out automatically, using computer software appropriate to that purpose.

In embodiments, methods are provided for detecting one or more of the presence, surface density and nature of the complement proteins on the surface of the B-lymphocytes of a subject. The method, which in some embodiments may be implemented by a processing device or system, implements a method that includes receiving a set of blood sampling data for a patient. The set of blood sampling data includes the level of one or more cell-bound complement activation products (CB-CAPs) for the patient. The method includes accessing a control data set that includes a control level for each of the CB-CAPs that is measured. The method includes comparing the CB-CAP levels for the patient with the control levels to determine a number and/or level (magnitude) of the CB-CAPs for which the patient's levels are elevated as compared to the control levels.

In embodiments of methods, systems and kits described herein, CB-CAPs may include one or more of: B-C4d, B-C3d, B-C3b, B-C4b, B-iC3b, B-iC4b, or B-C3dg.

Optionally, methods and systems may include determining a magnitude for one or more of the B-cell CB-CAPs for which an elevated level is present. In embodiments, the determined magnitude for one or more of the CB-CAPs may be used to determine whether to classify the patient as more or less likely to benefit from treatment with one or more antibodies, based on the binding characteristics of the antibody.

In embodiments, conditions that may be treated with antibody therapy include, but are not limited to, B-cell lymphoma, as well as systemic lupus erythematosus (SLE), rheumatoid arthritis, Sjogrens syndrome, systemic sclerosis, vasculitis, mixed cryoglobulinemia, inflammatory myopathies, and other autoimmune disorders.

In an embodiment, this document discloses a method of identifying a subject that is likely to derive therapeutic benefit from treatment with a particular antibody. The method, which in some embodiments may be implemented by a processing device or system, implements a method that includes receiving a set of blood sampling data for a patient. The set of blood sampling data includes the level of one or more cell-bound complement activation products (CB-CAPs) for the patient. The method includes accessing a control data set that includes a control level for each of the CB-CAPs that is measured. In embodiments, the method may include comparing the CB-CAP levels for the patient with the control levels to determine a number and/or level (magnitude) of the CB-CAPs for which the patient's levels are elevated as compared to the control levels. In embodiments, the method may use the determined number and/or level to assign a probability that the patient is likely to benefit from treatment with a particular antibody. In embodiments, the method may include generating a report comprising a diagnosis based on the probability.

In an embodiment, a method of determining whether a patient is likely to benefit from a particular antibody therapy includes, optionally by a processing device: (i) receiving a set of blood sampling data for a patient, wherein the set of blood sampling data includes one or more of cell-bound complement activation product (CB-CAP) levels associated with B-cells for the patient; (ii) accessing a control data set that includes a control level for each of the CB-CAPs; (iii) comparing the B-Cell CB-CAP levels for the patient with the control levels to determine whether one or more of the patient's B-Cell CB-CAPs levels are elevated as compared to the control levels; and (iv) generating a report comprising an indication of whether the patient is classified as having elevated CB-CAP levels on B-cells. Levels of B-Cell CB-CAPs may be correlated with changes in the binding affinity of one or more antibodies to their targets.

In an embodiment, a method of determining whether a subject is likely to benefit from therapy with an antibody, comprises, in a blood sample containing white blood cells from the subject: quantitating a level of at least one biomarker associated with a surface of a B lymphocyte in the sample, wherein the biomarker is selected from the group consisting of C4d, C3d, C4b, iC4b, C3b, iC3b, and C3dg; and comparing the levels of the biomarker for the subject with a level of the biomarker associated with a surface of a B lymphocyte of a control sample to determine a number of the biomarkers for which the subject's levels are elevated as compared to the control levels, wherein an increased level of the biomarker in the blood sample from the subject as compared to the level for the control, identifies the subject as less likely to respond favorably to treatment with a particular antibody.

In another embodiment, a method of determining whether to treat a patient with an antibody therapy includes, optionally by a processing device: (i) receiving a set of blood sampling data for a patient wherein the set of blood sampling data comprises at least one cell-bound complement activation product (CB-CAP) level associated with B lymphocytes of the patient; (ii) accessing a control data set, the control data set comprising a control level for each of the CB-CAPs; (iii) comparing the CB-CAP levels for the patient with the control levels to determine a number of the CB-CAPs for which the patient's levels are elevated as compared to the control levels; (iv) if the determined number exceeds a threshold, classifying the patient as not likely to benefit from antibody therapy; and (v) generating a report comprising an indication of whether the patient is classified as less likely to benefit from antibody therapy. In such cases, the method may be used to indicate that alternative antibody treatment may be more effective for a particular patient.

In another embodiment, a system for determining whether a patient is likely to benefit from an antibody therapy includes a processing device, a computer-readable medium, and a data storage facility holding a control data set of blood sampling data for a control subject population, and wherein the blood sampling data includes levels of one or more cell-bound complement activation products (CB-CAPs) for the patient. The computer-readable medium contains programming instructions that are configured to instruct the processing device to: (i) receive a set of blood sampling data for a patient, wherein the set of blood sampling data comprises CB-CAP levels for the patient, wherein the CB-CAP levels are for at least one of the following CB-CAPs: B-C4d, B-C3d, B-C3b, B-C4b, B-iC3b, B-iC4b, or B-C3dg; (ii) compare the CB-CAP levels for the patient with the control levels to determine the CB-CAPs for which the patient's levels are elevated as compared to the control levels; (iii) if the determined level of the patient's CB-CAPs are elevated above a threshold, classify the patient as less likely to benefit from antibody therapy; and (iv) generate a report comprising an indication of whether the patient is likely to benefit from the antibody therapy.

In embodiments, measurement of CB-CAPs associated with B lymphocytes of a patient may be used to calculate the correct dosage of antibody treatment effective for the patient. It is believed that the detection of CB-CAPs above certain threshold levels may be useful in making treatment decisions relating to antibody therapy.

In various embodiments described in this document, levels of CB-CAPs on PBMC, such as B cells, may indicate that: 1) the patient is not likely to respond to a particular therapy and an alternative treatment should be used; this may spare the expense and/or potential serious side effects of a therapy that is anticipated not to be effective; or 2) the patient might require a higher dose of the particular therapy; or 3) the patient might require a lower dose of the particular therapy if the CB-CAPs actually enhance binding of the therapeutic to the cell or signal transduction across the cell membrane triggered by the therapeutic; or 4) the CB-CAPs might predict that a patient is more likely to experience a side effect of the therapy such as infection, malignancy, etc. and should be monitored more closely for such. In embodiments, various forms of treatment may be provided to the patient, at least in part, in view of the results provided by use of methods, systems, and kits described herein.

Another embodiment provides a kit for measurement of CB-CAPs associated with B lymphocytes of a subject. The kit can include an antibody which is reactive with a cell-surface marker for B lymphocytes. In embodiments, the cell-surface marker for B lymphocytes may be selected from the group including, but not limited to, CD5, CD19, CD20, CD21, CD22, CD23, CD25, CD40, CD69, CD70, CD79, CD80, CD85, CD86, CD137, CD138, CD252, and CD268.

In embodiments, the kit may include a fluorescently-labeled antibody reactive with a cell-surface marker for B lymphocytes. In embodiments, the antibody may be a monoclonal antibody. Any such kit may be suitable for, as disclosed herein, the identification of one or more biomarkers, which may include, but is not limited to, the inclusion within the kit of antibodies reactive to one or more CB-CAPs. In embodiments, the antibodies reactive to one or more CB-CAPs may be monoclonal antibodies. In embodiments, antibodies reactive to one or more CB-CAPs may be fluoro-conjugated. In embodiments, the kit may optionally include one or more biochemical reagent. In embodiments, the kits may optionally include instructions for use of the kit and the kit components in measuring the relevant biomarker(s).

In an embodiment, a kit may comprise:
- a fluorescently-labeled antibody reactive with a cell-surface marker for B lymphocytes;
- a fluorescently-labeled antibody reactive with at least one CB-CAP;
- optionally, one or more biochemical reagents; and
- optionally, instructions for use of the kit and the kit components in the identification of one or more biomarkers.

In embodiments, the methods, systems and kits described in this document may employ any suitable reagents for the detection and/or measurement of CB-CAPS s associated with B lymphocytes of a subject, including, but not limited to, those described herein above.

In embodiments, the methods, systems, and kits described in this document may be used as a companion diagnostic in conjunction with antibody therapy. In embodiments, the therapeutic antibody may be a monoclonal antibody. In embodiments, the antibody binds to a specific antigen on B lymphocytes. In embodiments, the methods, systems and kits described herein may be used as companion diagnostics with at least one antibody that targets a B-cell antigen. The B-cell antigen may be selected from the group including, but not limited to, CD5, CD19, CD20, CD21, CD22, CD23, CD25, CD40, CD69, CD70, CD79, CD80, CD85, CD86, CD137, CD138, CD252, and CD268. In embodiments, the antibody therapy may comprise, without limitation, rituximab, epratuzumab, ofatumumab, veltuzumab, ocrelizumab, or another anti-B cell monoclonal antibody-based therapeutic. In an embodiment, the antibody therapy may comprise an anti-CD20 antibody, such as, without limitation, rituximab. In an embodiment, the antibody therapy may comprise an anti-CD22 antibody, including, without limitation, epratuzumab.

The following examples serve to further illustrate various embodiments of the present invention.

Example 1

C4d-labeled B lymphocytes were generated in vitro using a previously defined protocol. Levels of C4d bound to B lymphocytes were measured using a multicolor flow cytometric assay. Briefly, peripheral blood leukocytes (PBLs) were prepared by gradient centrifugation using Ficoll Plus (GE Healthcare). After removing contaminating erythrocytes by hypotonic lysis, PBLs were washed with phosphate-buffered saline (PBS), resuspended in PBS containing 1% bovine serum, and aliquoted for antibody staining. Lymphocytes were distinguished from monocytes and granulocytes based on the expression of characteristic surface molecules and their unique features of forward (size)/side (granularity) scattering. Phycoerythrin- or phycoerythrin Cy5-conjugated mouse monoclonal antibodies (mAb)

reactive with lineage-specific cell surface markers (CD19 for B lymphocytes; BD Biosciences, San Diego, Calif.) were used in conjunction with anti-human C4d (mouse IgG1; reactive with C4d-containing fragments of C4; Quidel, San Diego, Calif.) that had been labeled with Alexa Fluor 488 using the Zenon antibody labeling kit (Invitrogen, Carisbad, Calif.).

After staining, cells were analyzed using a FACS Calibur™ flow cytometer and Cell Quest software (Becton Dickinson Immunocytometry Systems). To ensure the specificity of the antibody staining detected, leukocyte aliquots from each patient stained with mouse IgG of appropriate isotypes were routinely included in all experiments. All mAb were used at a concentration of 5 µg/ml. Levels of cell-bound C4d were expressed as specific median fluorescence intensity (SMFI), which was calculated as the C4d-specific median fluorescence intensity minus the isotype control median fluorescence intensity.

Figure 1B:
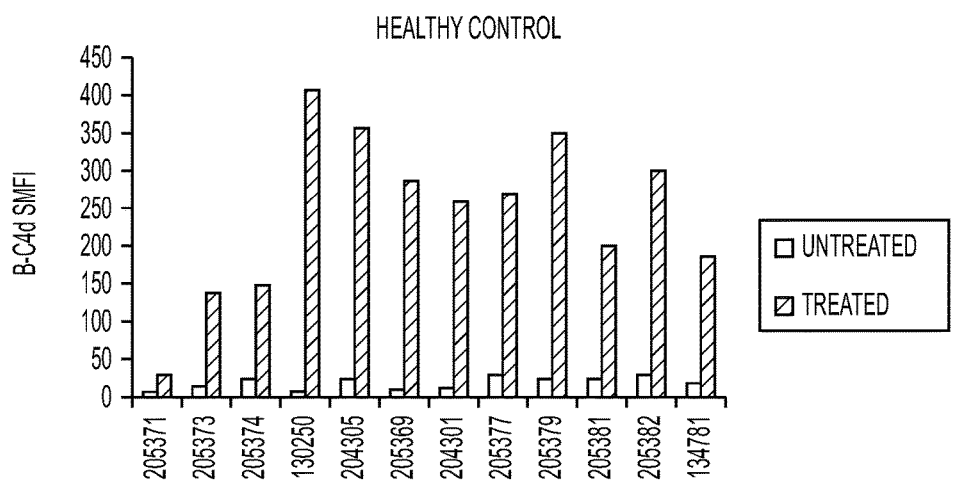

C4d-labeled B-cells were generated in vitro using plasma samples from four patients with Systemic Lupus Erythematosus (SLE) (FIG. 1(A) and 12 healthy controls (FIG. 1(B). FIG. 1 shows specific median fluorescence intensity (SMFI) achieved when labeled and unlabeled B-cells were treated with C4d antibodies. The results demonstrate that the present inventors have been successful in tagging B-cells with C4d.

Figure 2:
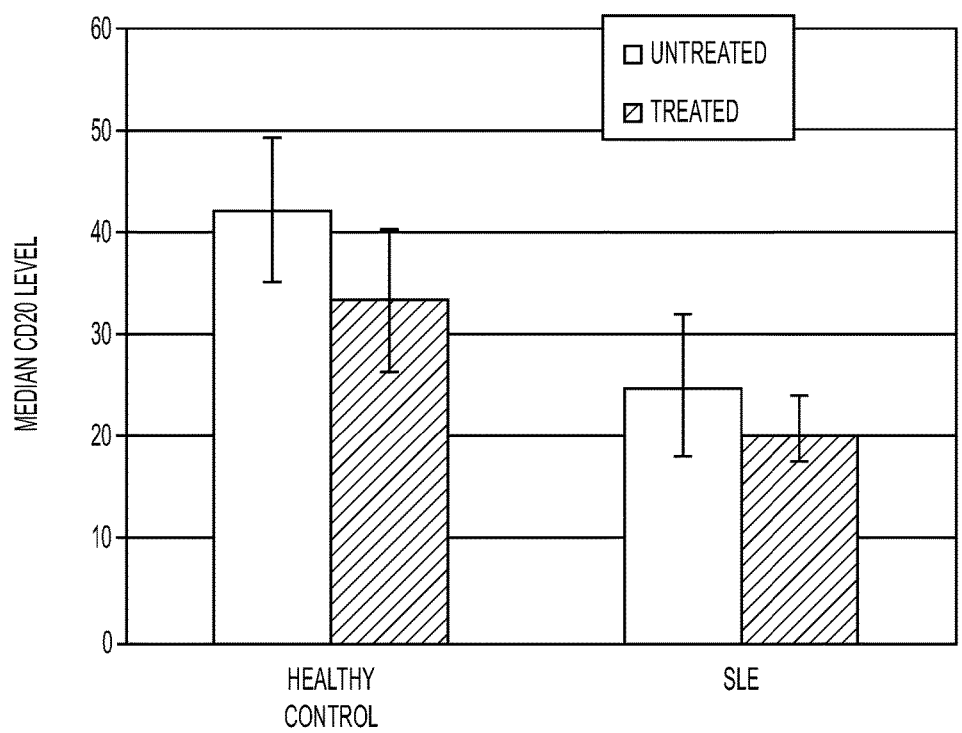
FIG. 2 illustrates that C4d-labeled B-cells were less effective in binding antibodies that targeted CD20 than were cells that were free of complement activation products.

Labeled and unlabeled cells from each patient sample were then treated with antibodies targeting CD20. As may be seen in FIG. 2, which shows SMFI for anti-CD20 antibody binding, C4d labeled cells were less effective in binding anti-CD20 antibodies than those not carrying complement activation products.

It is to be understood that this invention is not limited to the particular processes, compositions, or methodologies described, as these may vary. It is also to be understood that the terminology used in the description is for the purpose of describing some embodiments, and is not intended to limit the scope of the present invention.

Where features or aspects of the invention are described in terms of a Markush group or other grouping of alternatives, those skilled in the art will recognized that the invention is also thereby described in terms of any individual member or subgroup of members of the Markush group or other group.

Unless indicated to the contrary, all numerical ranges described herein include all combinations and subcombinations of ranges and specific integers encompassed therein. Such ranges are also within the scope of the described invention.

All references cited herein are incorporated by reference herein in their entireties.

The invention claimed is:

1. A method of estimating, for a subject, the binding of a potential therapeutic antibody directed against a B lymphocyte antigen, which comprises, in a blood sample containing white blood cells from the subject:
   quantitating a level of presence of at least one biomarker on a surface of a B lymphocyte in the sample, wherein the biomarker is selected from the group consisting of C4d, C3d, C4b, iC4b, C3b, iC3b, and C3dg; and
   comparing the level of presence of the biomarker for the subject with the level of presence of the biomarker on a surface of a B lymphocyte of a control sample to determine whether the subject's level of presence of the biomarker is elevated as compared to the level of presence in the control sample,
   correlating an increased level of presence of the biomarker in the blood sample from the subject as compared to the level of presence for the control sample with a decreased binding of the potential therapeutic antibody directed against the B lymphocyte antigen on the B lymphocytes of the subject, wherein the increased level of presence of the biomarker is detected before the administration of the potential therapeutic antibody treatment to the subject and without reference to the expression of the B lymphocyte antigen targeted by the potential therapeutic antibody.

2. The method of claim 1 wherein the biomarker is C4d.

3. The method of claim 1, wherein the B lymphocyte antigen is selected from the group consisting of CD5, CD19, CD20, CD21, CD22, CD23, CD25, CD40, CD69, CD70, CD79, CD80, CD85, CD86, CD137, CD138, CD252, and CD268.

4. The method of claim 1, wherein the control sample is a sample obtained from the subject at an earlier time.

5. The method of claim 1, wherein decreased binding of the potential therapeutic antibody directed against the B lymphocyte antigen on the B lymphocytes of the subject identifies the subject as less likely to respond favorably to treatment with the potential therapeutic antibody.

6. The method of claim 1, wherein:
   the subject is suspected of having an autoimmune disease or autoimmune disorder or is screened for an autoimmune disease or autoimmune disorder; and
   the control sample is derived from a control set of one or more individuals who do not suffer from the autoimmune disease or autoimmune disorder.

7. The method of claim 6, wherein the autoimmune disease or autoimmune disorder is selected from the group consisting of systemic lupus erythematosus (SLE), rheumatoid arthritis, Sjogrens syndrome, systemic sclerosis, vasculitis, mixed cryoglobulinemia, and inflammatory myopathy.

8. The method of claim 1, wherein:
   the subject is suspected of having an autoimmune disease or autoimmune disorder; and
   the control sample is derived from a control set of one or more individuals who have the autoimmune disease or autoimmune disorder, but who are not experiencing an acute phase of the autoimmune disease or autoimmune disorder.

9. The method of claim 8, wherein the autoimmune disease or autoimmune disorder is selected from the group consisting of systemic lupus erythematosus (SLE), rheumatoid arthritis, Sjogrens syndrome, systemic sclerosis, vasculitis, mixed cryoglobulinemia, and inflammatory myopathy.

10. The method of claim 1, wherein:
   the subject is suspected of having B-cell lymphoma or is screened for B-cell lymphoma; and
   the control sample is derived from a control set of one or more individuals who do not suffer from B-cell lymphoma.

* * * * *